US009308417B2

(12) United States Patent
Grundy (10) Patent No.: US 9,308,417 B2
(45) Date of Patent: Apr. 12, 2016

(54) METHOD AND SYSTEM FOR IDENTIFICATION OF CONCURRENTLY MOVING BODIES AND OBJECTS

(71) Applicant: Richard Grundy, Miami Beach, FL (US)

(72) Inventor: Richard Grundy, Miami Beach, FL (US)

(73) Assignee: FLOMIO, Miami Beach, FL (US)

( * ) Notice: Subject to any disclaimer, the term of this patent is extended or adjusted under 35 U.S.C. 154(b) by 0 days.

(21) Appl. No.: 14/332,500

(22) Filed: Jul. 16, 2014

(65) Prior Publication Data

US 2016/0023043 A1   Jan. 28, 2016

(51) Int. Cl.

| A63B 71/00  | (2006.01) |
|---|---|
| A63B 24/00  | (2006.01) |
| A63B 53/00  | (2015.01) |
| A63B 49/00  | (2015.01) |
| A63B 59/00  | (2015.01) |
| A63B 69/00  | (2006.01) |
| A63B 21/072 | (2006.01) |
| A63B 21/06  | (2006.01) |
| A63B 21/055 | (2006.01) |

(52) U.S. Cl.
CPC ........... *A63B 24/0062* (2013.01); *A63B 21/055* (2013.01); *A63B 21/06* (2013.01); *A63B 21/0724* (2013.01); *A63B 21/0726* (2013.01); *A63B 21/4035* (2015.10); *A63B 24/0003* (2013.01); *A63B 49/00* (2013.01); *A63B 53/00* (2013.01); *A63B 59/00* (2013.01); *A63B 69/0024* (2013.01); *A63B 2024/0065* (2013.01); *A63B 2220/40* (2013.01)

(58) Field of Classification Search
CPC .. A63B 21/055; A63B 21/06; A63B 21/0724; A63B 21/0726; A63B 21/4035; A63B 24/0062; A63B 24/0003; A63B 24/00; A63B 24/0021; A63B 2024/0009–2024/0071; A63B 49/00; A63B 53/00; A63B 59/00; A63B 69/0024
USPC .................................... 482/1, 8, 9, 901, 902
See application file for complete search history.

(56) References Cited

U.S. PATENT DOCUMENTS

| 5,474,083 | A  | * | 12/1995 | Church ................. A61B 5/486 600/546 |
|---|---|---|---|---|
| 6,013,007 | A  | * | 1/2000  | Root .................. A63B 24/0006 482/8 |
| 6,347,290 | B1 | * | 2/2002  | Bartlett ................ G06F 1/1626 702/150 |
| 8,740,752 | B2 |   | 6/2014  | Ellis et al. |
| 8,764,651 | B2 |   | 7/2014  | Tran |
| 8,768,865 | B2 |   | 7/2014  | Narayanan et al. |
| 8,771,148 | B2 |   | 7/2014  | Balakrishnan et al. |
| 8,776,171 | B2 |   | 7/2014  | Piersol |
| 2001/0011025 | A1 | * | 8/2001 | Ohki ...................... H04B 1/086 455/556.1 |
| 2004/0263473 | A1 | * | 12/2004 | Cho ........................ G06F 3/014 345/156 |
| 2009/0069156 | A1 |   | 3/2009  | Kurunmaki et al. |
| 2009/0210078 | A1 |   | 8/2009  | Crowley |
| 2010/0167646 | A1 |   | 7/2010  | Alameh et al. |
| 2014/0330186 | A1 | * | 11/2014 | Hyde ....................... A61F 5/02 602/19 |

\* cited by examiner

*Primary Examiner* — Stephen Crow
*Assistant Examiner* — Garrett Atkinson
(74) *Attorney, Agent, or Firm* — Marc Boillot (57) ABSTRACT

Herein provided is a method and system for wearable data collection in sports strength training and fitness exercise. The system includes an admin sensor set including sensors that couple to fitness equipment and a fitness sensor set which includes a wrist band sensor. A fitness app communicates with the sensors via Bluetooth Low Energy and Near Field Communication and detect concurrent movement based on proximity, user parameters and fitness object parameters. A fitness training report is generated that identifies the fitness objects used in a fitness exercise detected. Other embodiments are disclosed.

23 Claims, 8 Drawing Sheets

FIG. 1A

FITNESS SENSOR SET

ADMIN SENSOR SET

ADMIN APP
200

FIG. 2

FITNESS APP
300

METHOD AND SYSTEM FOR IDENTIFICATION OF CONCURRENTLY MOVING BODIES AND OBJECTS

FIELD

The present invention relates generally to wearable fitness devices, and particularly to identification and detection of fitness equipment and sports activity.

BACKGROUND

The fitness wearable device space has become popular due to the proliferation of mobile phones with low power wireless interfaces such as Bluetooth Low Energy (hereinafter BLE), Near Field Communication (hereinafter NFC), and Wifi Direct. Accessories like pedometers, heart rate monitors, and smart glasses leverage the Personal Area Network around the mobile device to enable powerful health and fitness solutions. One class of wearable pedometers attempt to detect the wearer's activity by pattern matching their motions against a database of known exercises. This approach can identify the exercise and number of repetitions carried out, but falls short in capturing the equipment used; for instance, weights lifted at a gym or the clubs swung on a golf course.

Methods exist for connectable devices to identify themselves via a pairing process. In one case, patent US20100167646A1, a pairing code is generated on each device as a result of motion data captured during the pairing period. Only the pairing code rather than the motion data is exchanged between devices. This is not a viable option for equipment identification because putting devices into pairing mode, generating pairing codes over a set period of time, and limiting the identification to only one device per period is too intrusive for what it's worth. A fitness session requires a more seamless experience where the identification of fitness objects is invisible to users.

DETAILED DESCRIPTION

While the specification concludes with claims defining the features of the embodiments of the invention that are regarded as novel, it is believed that the method, system, and other embodiments will be better understood from a consideration of the following description in conjunction with the drawing figures, in which like reference numerals are carried forward.

As required, detailed embodiments of the present method and system are disclosed herein. However, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the embodiments of the present invention in virtually any appropriately detailed structure. Further, the terms and phrases used herein are not intended to be limiting but rather to provide an understandable description of the embodiment herein.

The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "processor" can be defined as any number of suitable processors, controllers, units, or the like that carry out a pre-programmed or programmed set of instructions. The terms "program," "software application," and the like as used herein, are defined as a sequence of instructions designed for execution on a computer system. A program, computer program, or software application may include a subroutine, a function, a procedure, an object method, an object implementation, an executable application, an app, a source code, an object code, a shared library/dynamic load library and/or other sequence of instructions designed for execution on a computer system.

The following description of at least one exemplary embodiment is merely illustrative in nature and is in no way intended to limit the invention, its application, or uses. Similar reference numerals and letters refer to similar items in the following figures, and thus once an item is defined in one figure, it may not be discussed for following figures.

Figure 1A:
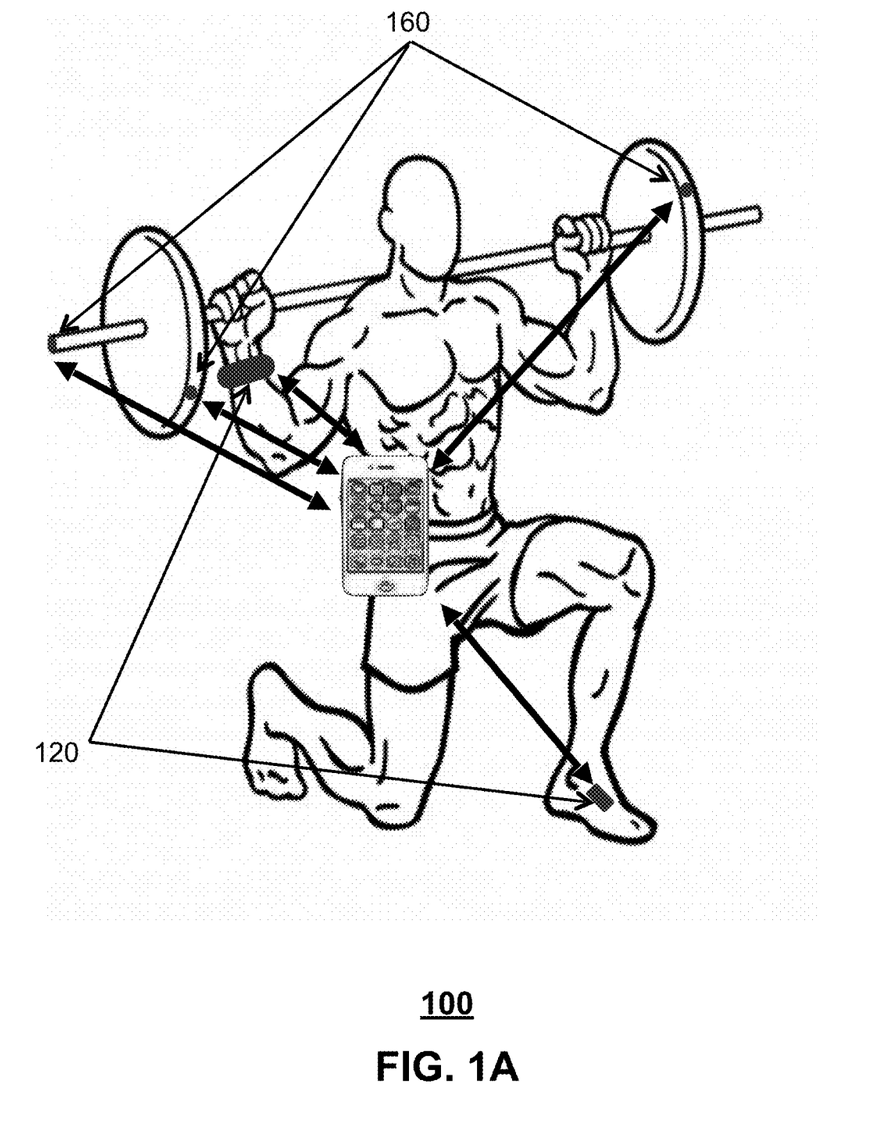
FIG. 1A depicts an exemplary illustration 100 of a system for wearable data collection in sports strength training and fitness in accordance with one embodiment.

Referring to FIG. 1A a system 100 for wearable data collection in sports strength training and fitness exercise. The system 100 includes a fitness sensor set 120 and an admin sensor set 160. Although shown for use in weight lifting, the system 100 can be used in conjunction with any other sports strength training, for example, golf, baseball, tennis, hockey, or lacrosse. As will be described ahead the system 100 includes wearable sensor devices for example those on a wrist, arm, or leg and fitness object sensors, for example, stickers and labels on weight training equipment. The method and system can further identify which instruments or fitness objects were used in a fitness activity. This is valuable in tracking progress, muscle endurance, calories burned, and power output. A user can then manage a more focused workout and maximize their overall performance.

With the advent of low power wireless interfaces offering connectionless data exchange, the system 100 by way of the sensors described ahead are now capable of interacting with mobile devices in close proximity without the computational overhead of secure connection establishment. The standards-based protocols have introduced well defined profiles that allow accelerometer data to be streamed to neighboring devices in real time. In one embodiment, the system listens for these streams and compares them to natively measured accelerometer data to find a match. Techniques for optimizing the solution for low power sensors are employed. As one example, sensors only advertise once motion is detected above a threshold and for a sustained period. Moreover, all streams of motion data are normalized based on sensor orientation, for example, by the gravity vector. And finally, a cloud-connected app is configured with the system to only receive streams from labeled instruments (weights, clubs, bats, rackets, etc).

Currently the most inexpensive technologies to identify an object are barcode, magnetic stripe, and RFID. Each of these carry a level of friction beyond what today's consumer would appreciate. BLE offers a more seamless alternative, however exhibits poor performance when trying to distinguish one asset from many in close proximity. The novel aspects of the inventive embodiments described herein by way of system 100 address this problem, allowing for many BLE motion sensors to be in range and filtering out all but those that are moving in unison with the subject's fitness sensor set. Consequently the method and system taught herein for mobile synchronization and data collection among devices can be used to calculate from the sensor data a fitness training report that identifies the fitness objects used in a fitness exercise, in addition to determining exercise and number of repetitions and capturing labeled instruments.

The system 100 targets the strength training (weights, fitness machines, resistance bands) and double pendulum sports instruments (clubs, bats, rackets, sticks, etc.), and can also be used to identify any motion synchronized set of assets. The coupling of the sensors and assets need not be along the same axis, either. Assets coupled through pulleys and other linearly dependent systems are detectable with the methods described herein. For instance, a fitness machine could have weights lifted vertically while the exercise involves horizontal displacement and still be recognized.

Figure 1B:
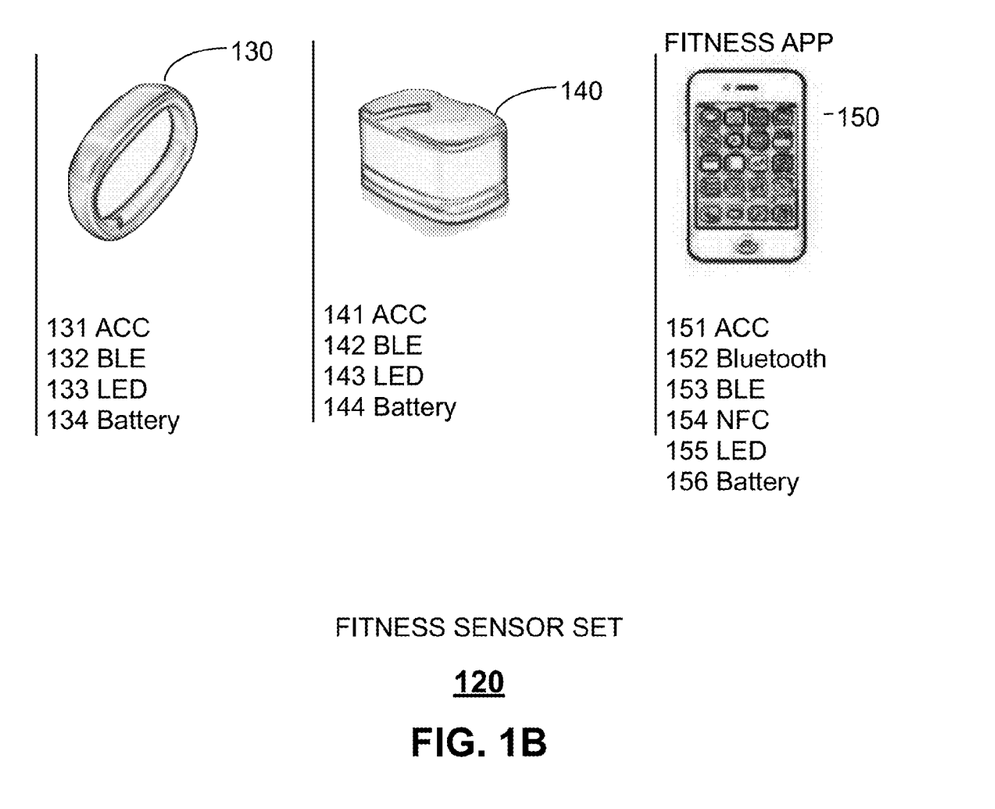
FIG. 1B depicts a fitness sensor set 120 comprising wearable devices, and a fitness app for the system of FIG. 1 in accordance with one embodiment.

As shown in FIG. 1B, the fitness sensor set 120 includes a wristband sensor 130 and a shoe clip sensor 140. The wristband sensor 130 identifies user parameters including motion and orientation of the wristband sensor 130. The shoe clip sensor 140 identifies user parameters including motion and orientation of the shoe sensor 140. Although referred to as a clip sensor, it may be an attachable sensor, such as one that inserts or attaches to the shoe. A fitness app 150 for coupling to the fitness sensor set 120 is provided that communicatively couples to the wristband sensor 130 and the shoe sensor 140.

The wristband sensor 130 includes an accelerometer 131, a BLE transceiver 132, a visual indicator 133 (e.g., light emitting diode—hereinafter LED) and a battery 134. The battery 134 powers the BLE 132, the accelerometer 131 and the LED 133. The BLE 132 transmits accelerometer data to the fitness app 150. It should be noted the BLE transmits accelerometer data to the fitness app 150 only upon it detecting its own motion. It is configured to transmit responsive to movement; it does this to conserve power. The visual indicator 133 indicates a status, for example, when configuring the wristband 130 by way of the fitness app 150 to enter user information, for example, which hand it is on (left or right) and arm length, as discussed ahead, and to let the user know which device is selected. In other embodiments the aspects of the wristband sensor 130 can be encapsulated, or integrated with, a wrist watch. In another arrangement, the sensor devices can be included in a headband. The wristband sensor 130 is waterproof and includes capabilities for wireless charging, for example, by way of an NFC enabled phone or reader functioning as a wireless charger.

The shoe clip sensor 140 includes an accelerometer 141, a BLE transceiver 142, a visual indicator 143 and a battery 144. The battery powers the BLE, the accelerometer, and the LED. It should be noted the BLE transmits accelerometer data to the fitness app 150 only upon it detecting its own motion. It is configured to transmit responsive to movement; it does this to conserve power. The visual indicator indicates a status, for example, if it is being configured with user parameters or updated, for example, when configuring the shoe sensor 140 by way of a fitness app 150 to enter user information, for example, which leg it is on (left or right) and leg length, as discussed ahead, and to let the user know which device is selected. In other embodiments the aspects of the shoe sensor 140 can be encapsulated, or integrated within, the shoe, for example, the shoe sole, inserts, or in the heel. The shoe clip sensor 140 is waterproof and includes capabilities for wireless charging, for example, by way of an NFC enabled phone or reader functioning as a wireless charger.

The fitness app 150 couples to the wristband sensor 130 and the shoe sensor 140. In certain embodiments only one of the sensors may be present. The fitness app 150 is a graphical user interface (GUI) that allows the user of the wristband and shoe sensor to interaction and configuration. As an example, the fitness app 150 allows the user to enter in wearable information. It is described ahead in further drawings; it can be installed and run on any suitable mobile device with a processor. The fitness app 150 is installed and runs on a mobile device which includes an accelerometer 151, a BLE transceiver 153 (may also be referred to as BLE herein), an NFC transceiver 154 (may also be referred to as NFC herein), a visual indicator LED 155, and a battery 156. The battery powers the BLE, the NFC, the accelerometer, and the LED. The mobile device exposes certain device functionalities and capabilities to the fitness app 150 for processing, receiving and transmitting sensor data.

The Bluetooth module 152 on the host mobile device exposing the fitness app 150 may comprise suitable logic, circuitry, interfaces and/or code that may be enabled to transmit and/or receive signals over the Bluetooth air-interface. The Bluetooth module 152 may be enabled to communicate the signals with the processor for further processing. Bluetooth is a low-power, short-range wireless networking standard designed for local area voice and data transfer. Bluetooth radios operate in the unlicensed ISM band at 2.4 GHz with a set of 79 hop carriers with 1 MHz spacing. A master-slave communication model with frequency hopping spread spectrum (FHSS) transmission technique is adopted in the Bluetooth specification to ensure protection from interference and security of data.

BLE is a ultra low power Bluetooth protocol for small, button cell battery-powered devices, such as, for example, watches, wireless keyboards, and gaming and sports sensors. These BLE devices may connect to Bluetooth-enabled host devices, whether computers or mobile phones. The host devices may also be some new devices designed for communicating with BLE devices for medical, sports, fitness, and watch markets, for example.

The Near Field Communication (NFC) module 154 enables faster and more intuitive interaction between two devices (e.g., wristband 130 and mobile device) and it is complimentary to Bluetooth, BLE, RFID and WiFi wireless networks. NFC can be used to instantly configure two devices to connect using long range wireless networks like Bluetooth or WiFi, without requiring the complex set-up procedure normally involved to initiate them. The host device on which the fitness app 150 runs comprises wireless short-range capabilities, for example Bluetooth, BLE, or NFC capabilities, the apparatus may receive user identity module related information via the wireless short-range capability. Similarly, in one embodiment, the apparatus may send user identity module related information via the wireless short-range communication capability. In one embodiment, the at least one short-range communication capability comprises at least one of a frequency modulation (FM) radio capability, amplitude modulation (AM) capability, a wireless short-range communication capability, a near field communication (NFC) capability, and a radio frequency identification (RFID) capability.

NFC is a short range wireless communication network that can be used by two devices supporting the NFC Standard to communicate with each other over a short range (20 cm, practically around 4 cm). NFC offers the ability to send small bits of data from a handset to a machine that is able to read that information, and process it. It allows the sensor devices to establish peer-to-peer radio communications, passing data from one device to another by touching them or putting them very close together. Near Field Communication (NFC) operates in the 13.56 MHz frequency band and currently supports data rates of 106 Kbps to 424 Kbps. NFC is a very short range communication network and the messages exchanged between two NFC enabled devices are encrypted; the protocol is relatively secure.

Figure 1C:
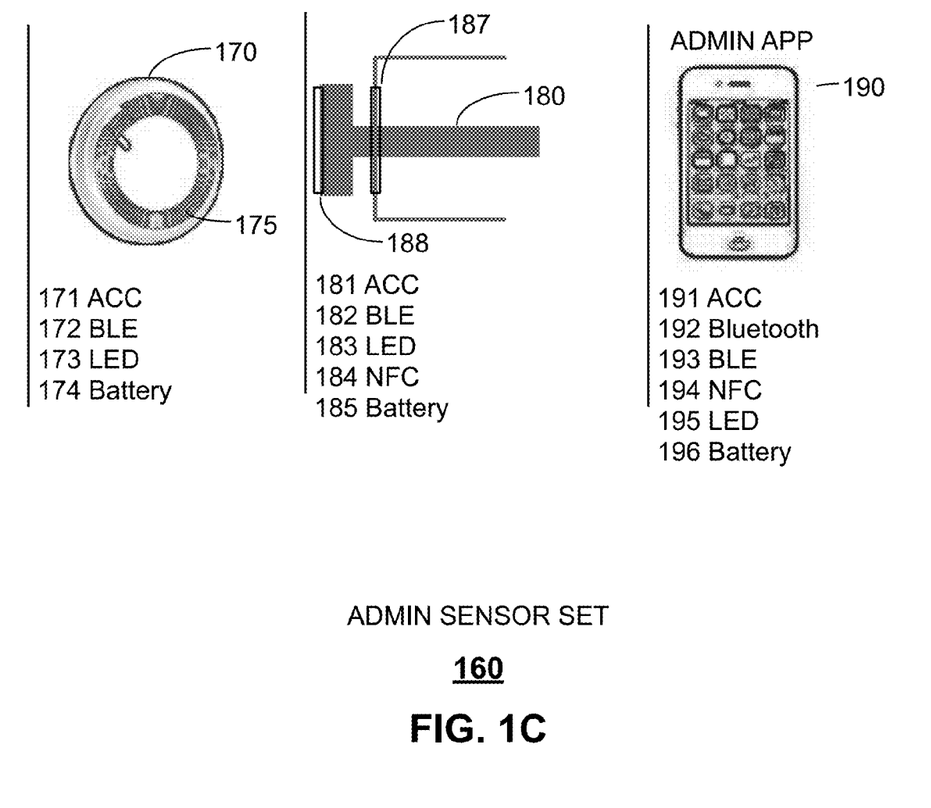
FIG. 1C depicts an admin sensor set 160 comprising sensors and labels that attach to fitness equipment, and an admin app for the system of FIG. 1 in accordance with one embodiment.

As shown in FIG. 1C, the admin sensor set 160 comprises a plurality of tag sensors 170 and a plurality of pin sensors 180. An admin app 190 is included for coupling to the admin sensor set 160 to communicate administrative data. The tag sensors 170 affix to a first set of fitness objects that identify object parameters including motion and orientation of the tag sensors 170. The first set of fitness objects can include at least one among a club, a racket, a bat, a hockey stick, a dumbbell, a plate, a bar, a bar bell, a cow bell, and a resistance band (also known as a resistance identifier which identifies the object, for example, the weight). The pin sensors 180 detachably couple to a second set of fitness objects and identify one or more second set object parameters including motion and orientation of the pin sensors. The second set of fitness objects can include at least one among a fitness machine grip, a fitness machine weight, a fitness machine resistance setting or other fitness equipment. For instance, in one embodiment, the pin sensor could replace the tension knob on a cycling machine in order to measure the total energy spent peddling by the subject.

Each tag sensor 170 includes an accelerometer 171, a BLE transceiver 172, a visual indicator LED 173 and a battery 174. The battery powers the BLE, the accelerometer and the LED. The BLE transmits accelerometer data to the fitness app. It should be noted the BLE transmits accelerometer data to the fitness app only upon it detecting its own motion. It is configured to transmit responsive to movement; it does this to conserve power. The visual indicator LED 173 indicates a status, for example, when configuring the sensor by way of the admin app 190 to enter fitness center information, for example, which strength training machine or weight to which the tag sensor 170 is affixed, as discussed ahead, and to let the admin know which device is selected for configuration. Furthermore, a passive tag 175 enables instant configuration of a tag sensor via the admin app NFC 194 without requiring, as discussed ahead, the complex set-up procedure normally involved to initialize them. In other embodiments the aspects of the tag sensor 170 can be encapsulated, or integrated with, the weight or a component of the fitness machine (e.g., slot, pulley, handle, knob, etc.).

Each pin sensor 180 includes an accelerometer 181, a BLE transceiver 182, a visual indicator LED 183, an NFC transceiver 184 and a battery 174. The battery powers the BLE, the accelerometer, the NFC and the LED. The NFC interface detects passive tags 187 affixed to each weight in a weight machine. It does this to capture which weight has been selected during an exercise. It should be noted the BLE transmits the passive tag selected and accelerometer data to the client app only upon it detecting its own motion. It is configured to transmit responsive to movement; it does this to conserve power. The visual indicator LED 183 indicates a status, for example, when configuring the sensor by way of the admin app 190 to enter fitness center information, for example, which strength training machine the pin sensor belongs to or weight to which the passive tag 187 is affixed, as discussed ahead, and to let the admin know which device is selected for configuration. Furthermore, a passive tag 188 enables instant configuration of a pin sensor via the admin app NFC 195 without requiring, as discussed ahead, the complex set-up procedure normally involved to initiate them. In one arrangement, the passive tags 187 are metal mount NFC inlays, built to last and no battery needed; where the pin sensors 180 only wakes when label (e.g., 187) is detected with timeout period.

The admin app 190 couples to the admin sensor set 160 that by way of an admin mobile device operatively connects to the plurality of tag sensors 170 and the plurality of pin sensors 180 to communicate fitness data. The admin app 190 is a graphical user interface (GUI) that allows the administrator of the admin sensor set 160 interaction and configuration. As an example, the admin may be the fitness center manager responsible for placing the sensors onto the weights in the gym, and entering in the weight information to which each fitness object the sensor is attached. It is described ahead in further drawings; the admin app 190 can be installed and run on any suitable mobile device with a processor.

The admin app 190 is installed and runs on a host mobile device which includes an accelerometer 191, a BLE transceiver 193, an NFC transceiver 194, a visual indicator LED 195, and a battery 156. The battery powers the BLE, the NFC, the accelerometer, and the LED. The Bluetooth module 192 on the host mobile device exposing the admin app 190 may comprise suitable logic, circuitry, interfaces and/or code that may be enabled to transmit and/or receive signals over the Bluetooth air-interface. The Bluetooth module 192 may be enabled to communicate the signals with the processor for further processing. The NFC module 194 enables fast and intuitive interaction between two devices (e.g., tag sensor 170 and mobile device) and it is complimentary to Bluetooth, BLE, RFID and WiFi wireless networks. NFC can be used to instantly configure two devices to connect using long range wireless networks like Bluetooth or WiFi, without requiring the complex set-up procedure normally involved to initiate them. The host device on which the admin app 190 runs comprises wireless short-range capabilities, for example Bluetooth and NFC capabilities.

Figure 2:
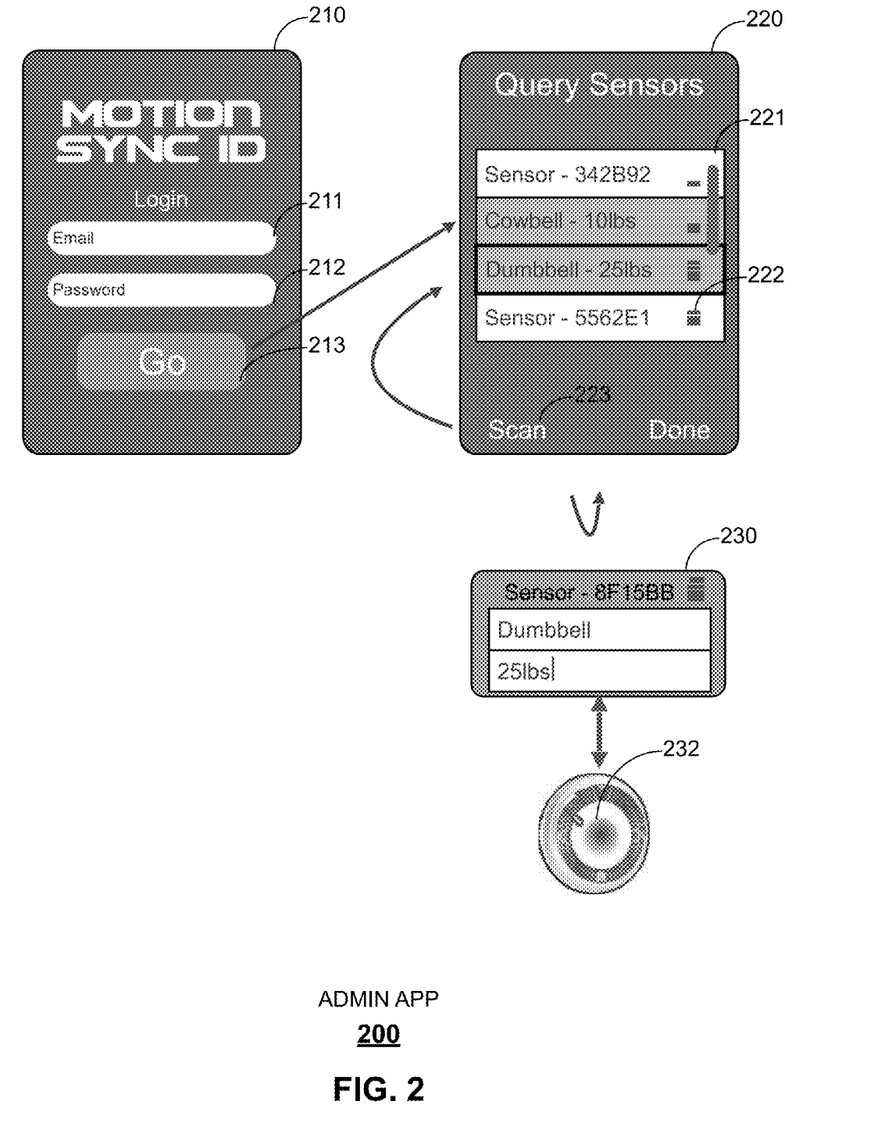
FIG. 2 depicts an exemplary illustration of a method 200 of fitness equipment set up and administration by an admin using the components shown in FIG. 10 in accordance with one embodiment.

FIG. 2 is an exemplary diagrammatic illustration for use of the admin app 190 in the context of fitness training administration. Recall, the admin app 190 is provided with the admin sensor set 160 to configure the tag sensors 170 and the pin sensors 180 with corresponding fitness training objects. For example, an administrator of the gym upon purchasing the admin sensor set 160 devices will proceed to place (install) each sensor on a piece of fitness equipment. This configuration of the fitness center by way of the admin app 190 is necessary in advance of use of the system 100 shown in FIG. 1 for wearable data collection in sports strength training and fitness exercise.

The admin app 190 is cloud-connected and requires an account to operate it. The administrator launches admin app 190 and enters the account information in fields 211 and 212 provided during purchase of the admin sensor set 160. Selecting the Go button 213 with proper account information allows for the admin sensor set to be managed 210. Scanning the environment 223 for the purchased admin sensor set lists all the sensors in range. Each entry in the list 221 shows the sensors unique identifier along with it's battery status 222. Selecting items on the list allows for establishing a connection with the sensor indicated by LED 232. When selected, modal dialog 230 allows for modification of meta data associated with this sensor, including name and weight. Although shown for use in weight lifting, the meta data 230 can be used in conjunction with any other sports objects, for example, golf clubs, baseball bats, tennis racquets, hockey sticks, or lacrosse sticks. Meta data may be customized for each of these activities.

Figure 3:
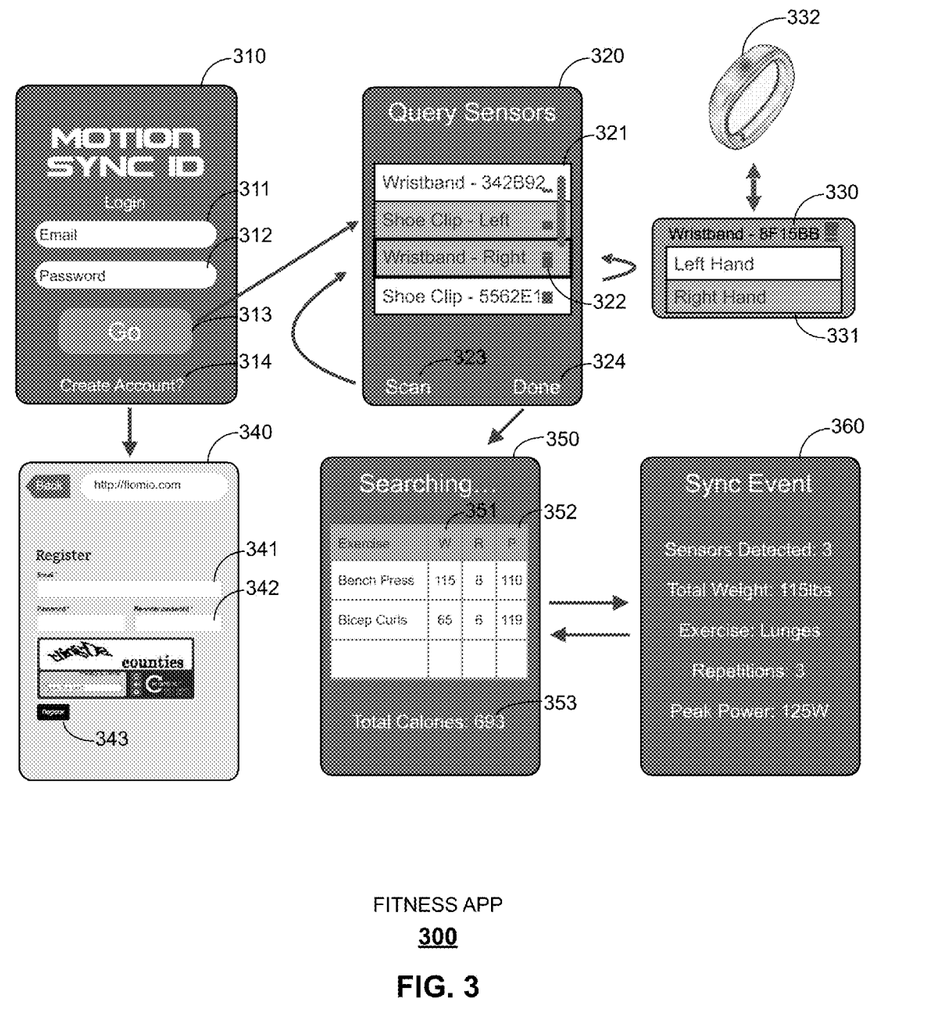
FIG. 3 depicts an exemplary illustration of a method 300 of fitness wearable use and activity by a user using the components shown in FIG. 1B in accordance with one embodiment.

FIG. 3 is an exemplary diagrammatic illustration for use of the fitness app 150 in the context of personal fitness training. Recall, the fitness app 150 is provided with the fitness sensor set 120 to personalize the wristband sensor 130 and the shoe sensors 140 for the user; that is, the person that will be doing the exercises. For example, a user member enrolled in the gym upon purchasing the fitness sensor set 120 devices will desire to receive a fitness training report that identifies the fitness objects used in a fitness exercise detected from the tag sensor selection set installed in the gym. Understandably, for wearable data collection in sports strength training and fitness exercise in accordance with system 100, it is necessary for the gym to be already equipped with an installation of the admin sensor set 160. The use of the admin app 190 in the context of fitness training administration was discussed above in FIG. 2.

The fitness app is cloud-connected and requires an account to operate it. The user launches client app 310 and enters the account information in fields 311 and 312 provided during purchase of the fitness sensor set 120. Selecting the Go button 313 with proper account information allows for the fitness sensor set to be managed 320. Scanning the environment 323 for the purchased fitness sensor set lists all the sensors in range. Each entry in the list 321 shows the sensor's unique identifier along with it's battery status 322. Selecting items on the list allow for establishing a connection with the sensor indicated by LED 332. When selected, modal dialog 330 allows for modification of meta data associated with this sensor, such as left or right hand. Although shown for use on the wrist, the meta data 330 can be used in conjunction any other sensors and locations such as left or right foot or headband or waist. Selecting Done 324 begins the process of recording a fitness training report in 350. The exercise weight 351 and power 352 is calculated based on sync events detected 360. It should be noted that sync events can be detected while the mobile device is unattended and the screen is off. Identified sensors are tabulated 350 and the motion data of the exercise is used to calculate the power generated 352. Total calories burned is calculated across all the sync event entries in the fitness training report 353.

Figure 4:
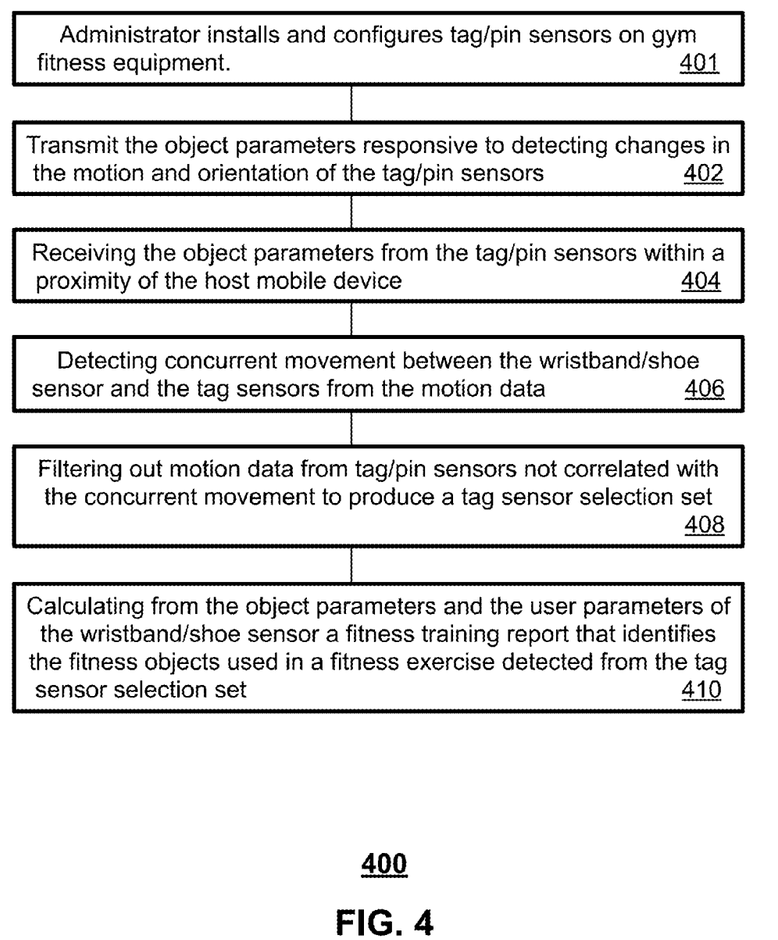
FIG. 4 is a method 400 for wearable data collection in sports strength training and fitness exercise in accordance with one embodiment.

Referring to FIG. 4, a method 400 for creating an interface is shown. The method 400 can be practiced with more or less than the number of steps shown. To describe the method 400, reference will be made to FIGS. 1A-C and FIGS. 2-3 although it is understood that the method 400 can be implemented in any other manner using other suitable components. Moreover, the method 400 is not limited to the order in which the steps are listed in the method 400. In addition, the method 400 can contain or be practiced with a greater or a fewer number of steps than those shown in FIG. 4.

At step 401 the method can start. The method can start in a state, for example, as illustrated in FIG. 1 where a user is performing a sports strength exercise utilizing the fitness sensor set 120, and where the fitness center has been set up and configured by an administrator with the admin sensor set 160.

At step 402, by way of the admin sensor set 160 including a plurality of tag sensors 170 that affix to a first set of fitness objects (e.g., weights, machines, handles, knobs) that identify object parameters (weight, size, machine ID, location, position, usage, etc.) including motion and orientation of the tag sensors, the sensors of the admin sensor set 160 transmit the object parameters responsive to detecting changes in the motion and orientation of the tag sensors. That is, the tag sensors 170 and pin sensors 180 and labels 187 (if present) only convey movement information, for example, the x,y,z values from the accelerometer, if a motion is detected. This is done to conserve battery energy. The object parameters include at least one among a weight, a machine identification, a placement identification, and a descriptive identifier of the tag sensor.

Briefly, each tag sensor 170 or pin sensor 180, upon itself detecting its own motion, performs the steps of creating a data packet that includes the object parameters and a recommendation entry for a non-servicing mode; and advertising for the non-servicing mode by way of the data packet. The recommendation entry may be 8 bytes of a 23 byte BLE advertising payload. That is, the tags advertise themselves for connectivity but recommend that devices do not connect to them, but rather, extract descriptive data from the packets, for example, just the accelerometer data. In this way, the mobile device does not set up a service agreement with the tag/pin sensors which would otherwise exclude the tags from visibility from other devices. This allows all tag/pin sensors to continuously transmit data (e.g., accelerometer data, object parameters) as frequently as every 100 ms to all devices and be heard by all devices. For instance, each x, y and z acceleration component represented by 7 bytes is transmitted in the advertised packet instead of in an established service link (which takes more time to set up). The Maximum Advertising Packet Length is generally set at 32 bytes for the BLE advertising packet, of which, there are approximately 23 bytes available for custom data insertion (e.g., accelerometer data, time data, user parameters, and object parameters). Approximately 9 bytes are required for the BLE transmission, including header codes and other identifiers.

Accordingly, the fitness app 150 listens to advertisement from the tag sensors and collects object parameters contained in the data packet, but does not formally establish a Bluetooth service connection to the tag sensor; that is, it does not enter into a handshake to establish a service link.

A more traditional approach is to have each tag sensor 170 or pin sensor 190 be connectable and expose a standard BLE accelerometer profile. This offers the benefits of standardized hardware to drive down the sensor prices as opposed to the customized firmware needed as previously discussed above. Nevertheless, host mobile devices with BLE 153 support can sustain at most 8 active sensor connections at once with parameter updates as frequent as every 20 ms. To support the identification of fitness sensor sets 120 and admin sensor sets 160 that amount to more than 8 BLE connections, a time division multiple access approach can be used. As sensors get identified per method 400, the host mobile device disconnects and seeks to connect to another sensor in a round robin pattern.

At step 404, by way of the fitness sensor set 120 including the wristband sensor that identifies user parameters (e.g., user name, contact info, personal data, left/right side, arm length, leg length, etc.) including motion and orientation of the wristband sensor 130, and the fitness app 150 on a host mobile device operatively coupled to the wristband and the tag sensors 170 that configures, collects and communicates fitness data, the host mobile device by way of the fitness app 150 receives the object parameters from the tag/pin sensors within a proximity of the wristband/shoe sensor. The user parameters include at least one among a left or right wristband placement and an arm length or leg length associated with the wristband.

At step 406, upon the fitness app receiving the object parameters from the tag sensors within a proximity of the wristband, the fitness app 150 by way of the host mobile device (e.g., cell phone, smart phone, tablet, etc.) detects concurrent movement between the wristband 130 and the tag sensors 170 (and pin sensors 180 if present) from the motion data. Concurrent movement is correlated movement with respect to either/or physical relations (up, down, left, right) according to metrics (distance, velocity, speed, direction, magnitude, vector) and/or with respect to identified exercise patterns, for example, associating motion trajectories of the wristband during lunges with the tag sensors 170 on the weights of the dumbbell (see FIG. 1 system 100). All sensors move together in a predictable pattern/manner during exercise to filter out neighboring sensors. Also, it should be noted that the fitness app 150 only looks for sensors moving within proximity (less than 50 meters of the user wearing the wristband).

The fitness app 150, at step 408, also filters out motion data from tag sensors not correlated with the concurrent movement to produce a tag sensor selection set. For example, it determines if tag sensors 170 (and pin sensors 180 if present) are produced by the same manufacturer, or under similar administration of the fitness center, and filter these out of any proceeding calculations. The tag selection set is the identified set of tag/pin sensors specific to the fitness program of the user, for example, those identified as potentially belonging to the user performing the exercise based on identified parameters (weight, size, etc.) and behaviors (back, forward, up, down).

At step 410, the fitness app 150 calculates from the object parameters and the user parameters of the wristband sensor (and shoe sensor if present) a fitness training report that identifies the fitness objects used in a fitness exercise detected from the tag sensor selection set. The fitness training report, from the calculation identifies the fitness objects by one among weight, size and description. The identified the fitness object is at least one among a club, a racket, hockey stick, a bat, a dumbbell, a plate, a bar, a bar bell, a cow bell, a band, a grip, a weight machine, a strength machine or fitness equipment, but not only limited to these.

Figure 5:
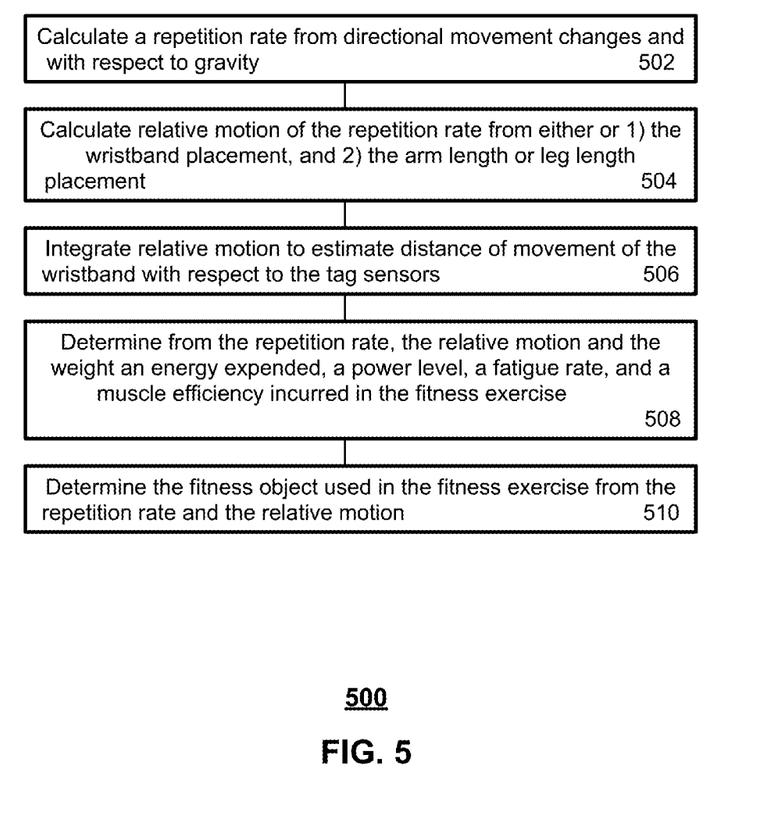
FIG. 5 is a method 500 for determining fitness objects used in sports training and fitness exercise in accordance with one embodiment.

Referring to FIG. 5, a method 500 for identifying fitness objects used is shown. The method 500 can be practiced with more or less than the number of steps shown. To describe the method 500, reference will be made to FIGS. 1A-C and FIGS. 2-3 although it is understood that the method 500 can be implemented in any other manner using other suitable components. Moreover, the method 500 is not limited to the order in which the steps are listed in the method 500 In addition, the method 500 can contain a greater or a fewer number of steps than those shown in FIG. 5.

The method 500 explains the step of calculating from the object parameters and the user parameters of the wristband sensor a fitness training report that identifies the fitness objects used in a fitness exercise detected from the tag sensor selection set described in step 410 of method 400.

At step 502, the fitness app 150 upon receiving the BLE packet (as previously explained by 'listening' for advertisement from the tag/pin sensors and wristband/shoe sensors), calculates a repetition rate from directional movement changes and with respect to gravity. The repetition rate describes, for example, how many times the user performed a routine, for instance, lifting weights, lunging, swinging, etc. The gravity information is available from the accelerometer data advertised by the sensors (tags, pins, wristband, shoe). Recall, the object parameters include at least one among a weight identifier, a machine identification, a placement identification, and a descriptive identifier. This information was provided during admin system set up (see FIG. 2) by way of the admin app 190. This information is used in conjunction with the positional/directional/acceleration/movement information received from the tag sensors 170 (and pin sensors 180 if present) and the wristband 130 (and shoe sensor if present).

At step 504, the fitness app 150 calculates a relative motion of the repetition rate from either/or 1) the wristband placement, and 2) the arm length or leg length placement. That is, it may do one, or the other, or both. Recall also, the user parameters include a left or right placement, and an arm length or leg length. This personal information was provided during user set up (see FIG. 3) by way of the fitness app 150. This information is used in conjunction with the repetition rate information and positional, directional, acceleration, movement information received from the tag sensors 170 (and pin sensors 180 if present) and the wristband 130 (and shoe sensor 140 if present).

At step 506, the fitness app 150 integrates the relative motion to estimate distance of movement of the wristband with respect to the tag sensors. It can do this from summation of the accelerometer data points over time. Thereafter at step 508, the fitness app 150 determines from the repetition rate, the relative motion and the weight at least one among an amount of energy expended, a power level, a fatigue rate, and a muscle efficiency incurred in the fitness exercise. And, at step 510, it then determines from the repetition rate and the relative motion the fitness object used in the fitness exercise. The fitness object may be a club, a racket, a bat, hockey stick, a dumbbell, a plate, a bar, a bar bell, a cow bell, a band, a grip, a weight machine, a strength machine or fitness equipment. And, the fitness training report, from the calculation identifies the fitness objects by one among weight, size and description.

Figure 6:
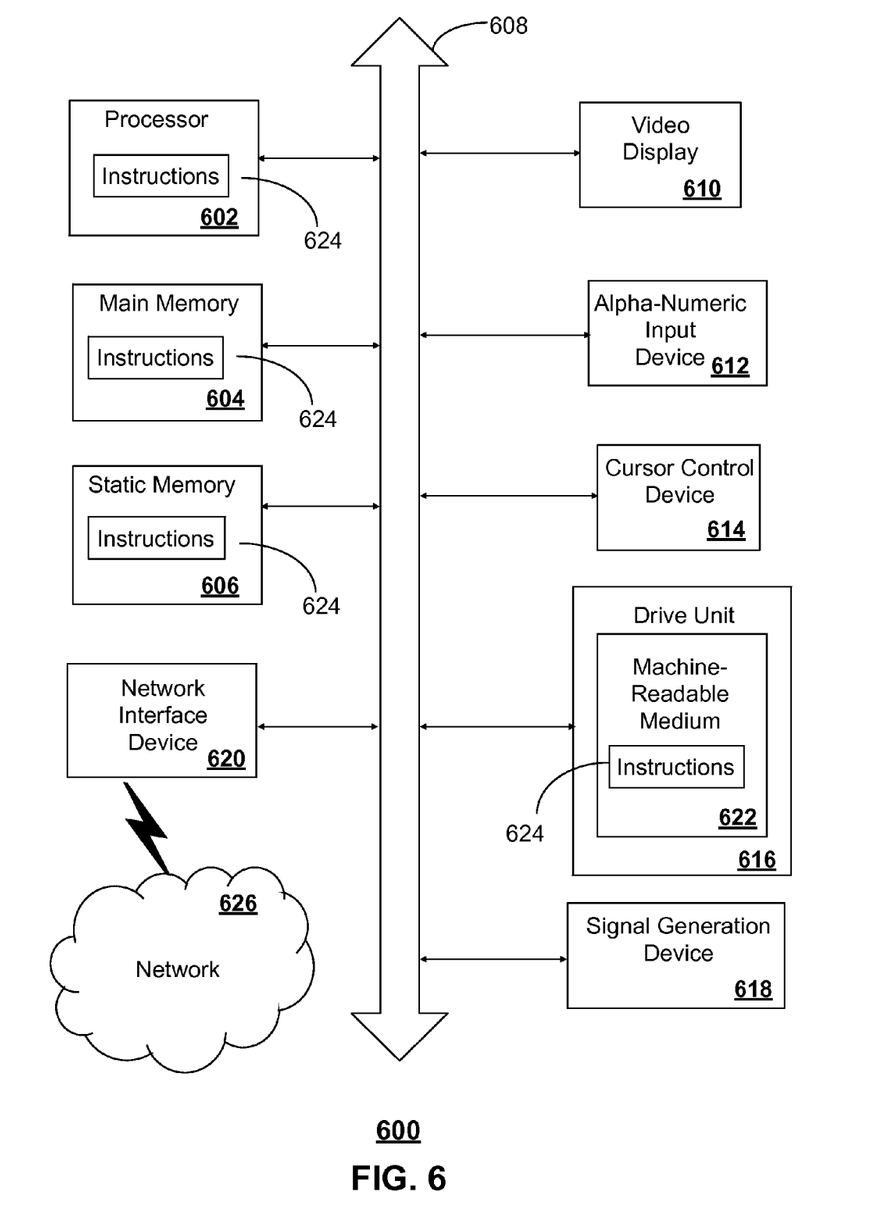
FIG. 6 depicts an exemplary diagrammatic representation of a machine 600 in the form of a computer system within which a set of instructions, when executed, may cause the machine to perform any one or more of the methodologies disclosed herein.

FIG. 6 depicts an exemplary diagrammatic representation of a machine in the form of a computer system 600 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 600 may include a processor 602 (e.g., a central processing unit (CPU), a graphics processing unit (GPU, or both), a main memory 604 and a static memory 606, which communicate with each other via a bus 608. The computer system 600 may further include a video display unit 610 (e.g., a liquid crystal display (LCD), a flat panel, a solid state display, or a cathode ray tube (CRT)). The computer system 600 may include an input device 612 (e.g., a keyboard), a cursor control device 614 (e.g., a mouse), a disk drive unit 616, a signal generation device 618 (e.g., a speaker or remote control) and a network interface device 620.

The disk drive unit 616 may include a machine-readable medium 622 on which is stored one or more sets of instructions (e.g., software 624) embodying any one or more of the methodologies or functions described herein, including those methods illustrated above. The instructions 624 may also reside, completely or at least partially, within the main memory 604, the static memory 606, and/or within the processor 602 during execution thereof by the computer system 600. The main memory 604 and the processor 602 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 624, or that which receives and executes instructions 624 from a propagated signal so that a device connected to a network environment 626 can send or receive voice, video or data, and to communicate over the network 626 using the instructions 624. The instructions 624 may further be transmitted or received over a network 626 via the network interface device 620.

While the machine-readable medium 622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

While the preferred embodiments of the invention have been illustrated and described, it will be clear that the embodiments of the invention are not so limited. Numerous modifications, changes, variations, substitutions and equivalents will occur to those skilled in the art without departing from the spirit and scope of the present embodiments of the invention as defined by the appended claims.

What is claimed is:

1. A system for wearable data collection in sports strength training and fitness exercise comprising:
   an admin sensor set including
      a plurality of tag sensors that affix to a first set of fitness objects that identify object parameters including motion and orientation of the tag sensors; and
   a fitness sensor set including
      a wristband sensor that identifies user parameters including motion and orientation of the wristband sensor; and
   a fitness app that by way of a host mobile device operatively couples to the wristband and the tag sensors to configure, collect and communicate fitness data,
   where the fitness app, upon detection of movement of the tag sensors and the wristband sensor:
      receives motion data from the tag sensors within a proximity of the wristband;

detects concurrent movement between the wristband and the tag sensors from the motion data;
filters out motion data from tag sensors not correlated with the concurrent movement to produce a tag sensor selection set;
calculates from the object parameters and the user parameters of the wristband a fitness training report that identifies the fitness objects used in a fitness exercise detected from the tag sensor selection set.

2. The system of claim 1, where the wristband sensor further an accelerometer, a Bluetooth Low Energy (BLE) transceiver, a battery and a visual indicator; where the battery powers the BLE transceiver, the accelerometer and the visual indicator, and the BLE transceiver transmits accelerometer data to the fitness app, and the visual indicator indicates a status.

3. The system of claim 1, where the fitness sensor set further includes a shoe clip sensor comprising an accelerometer, a BLE transceiver, a battery and a visual indicator; where the battery powers the BLE transceiver, accelerometer, and visual indicator, and the BLE transceiver transmits accelerometer data to the fitness app, and the visual indicator indicates a status.

4. The system of claim 1, where the admin sensor set includes an admin app that by way of an administrator mobile device operatively couples to the plurality of tag sensors and the plurality of pin sensors to communicate administrative data.

5. The system of claim 1, where the admin sensor set includes a plurality of pin sensors that detachably couple to a second set of fitness objects and identify one or more second set object parameters including motion and orientation of the pin sensors.

6. The system of claim 1, where for the admin sensor set:
each tag sensor includes an accelerometer, a BLE transceiver, a battery and a visual indicator; where the battery powers the BLE transceiver and the accelerometer, and the BLE transceiver transmits accelerometer data and the visual indicator indicates a status;
each pin sensor includes an accelerometer, a BLE transceiver, a battery, a visual indicator and an NFC transceiver where the battery powers the BLE transceiver, the NFC transceiver and the accelerometer, and the NFC transceiver collects NFC data from NFC labels on the second set of fitness objects, and the BLE transceiver transmits the NFC data and the accelerometer data and the visual indicator indicates a status.

7. The system of claim 1, where the user parameters include a left or right placement, and an arm length or leg length.

8. The system of claim 1, where the object parameters include at least one among a weight identifier, a resistance identifier, a machine identification, a placement identification, and a descriptive identifier.

9. The system of claim 8, where the fitness app listens to advertisement from multiple tag sensors and collects object parameters contained in the data packet, but does not establish a Bluetooth service connection to the tag sensor.

10. The system of claim 8, where the fitness app scans for multiple tag sensors, establishes a Bluetooth services connection to each in a round robin approach, and collects object parameters contained in the data packet.

11. The system of claim 1, where each tag sensor:
upon itself detecting its own motion;
creates a data packet that includes the object parameters and a recommendation entry for a non-servicing mode; advertises for the non-servicing mode by way of the data packet.

12. The system of claim 1, where each tag sensor:
upon itself detecting its own motion;
creates a data packet that includes the object parameters and a recommendation entry for a connectable mode;
notifies updates through an established connection by way of the data packet.

13. A method of data collection in sports strength training and fitness exercise that:
by way of an admin sensor set including
a plurality of tag sensors that affix to a first set of fitness objects that identify object parameters including motion and orientation of the tag sensors,
transmitting the object parameters responsive to detecting changes in the motion and orientation of the tag sensors; and
by way of a fitness sensor set including
a wristband sensor that identifies user parameters including motion and orientation of the wristband sensor,
a fitness app on a host mobile device operatively coupled to the wristband and the tag sensors that configures, collects and communicates fitness data,
upon the fitness app receiving the object parameters from the tag sensors within a proximity of the wristband,
detecting concurrent movement between the wristband and the tag sensors from the motion data;
filtering out motion data from tag sensors not correlated with the concurrent movement to produce a tag sensor selection set;
calculating from the object parameters and the user parameters of the wristband a fitness training report that identifies the fitness objects used in a fitness exercise detected from the tag sensor selection set.

14. The method of claim 13,
where the user parameters include at least one among a left or right wristband placement and an arm length or leg length associated with the wristband,
where the object parameters include at least one among a weight, a machine identification, a placement identification, and a descriptive identifier of the tag sensor.

15. The method of claim 14, wherein the step of calculating includes
calculating a repetition rate from directional movement changes and with respect to gravity;
calculating relative motion of the repetition rate from either or 1) the wristband placement, and 2) the arm length or leg length placement; and
integrating relative motion to estimate distance of movement of the wristband with respect to the tag sensors.

16. The method of claim 15, determining from the repetition rate, the relative motion and the weight at least one among an amount of energy expended, a power level, a fatigue rate, and a muscle efficiency incurred in the fitness exercise.

17. The method of claim 15, determining from the repetition rate and the relative motion the fitness object used in the fitness exercise.

18. The method of claim 15, wherein the fitness object is at least one among a club, a racket, a bat, hockey stick, a dumbbell, a plate, a bar, a bar bell, a cow bell, a resistance band, a grip, a weight machine, a strength machine or fitness equipment.

19. The method of claim 13, where the fitness training report, from the calculation identifies the fitness objects by one among weight, size and description.

20. The method of claim 13, where each tag sensor performs the steps of:
- upon itself detecting its own motion;
- creating a data packet that includes the object parameters and a recommendation entry for a non-servicing mode; and
- advertising for the non-servicing mode by way of the data packet.

21. The method of claim 13, where each tag sensor performs the steps of:
- upon itself detecting its own motion;
- creates a data packet that includes the object parameters and a recommendation entry for a connectable mode; and
- notifies updates through an established connection by way of the data packet.

22. The method of claim 20, where the fitness app listens to advertisement from the tag sensors and collects object parameters contained in the data packet, but does not establish a Bluetooth service connection to the tag sensor.

23. The method of claim 21, where the fitness app scans for multiple tag sensors, establishes a Bluetooth services connection to each in a round robin approach, and collects object parameters contained in the data packet.

* * * * *